(12) United States Patent
Ueda et al.

(10) Patent No.: US 9,855,411 B2
(45) Date of Patent: Jan. 2, 2018

(54) CONNECTOR AND INFUSION SET

(71) Applicant: TERUMO KABUSHIKI KAISHA, Shibuya-ku, Tokyo (JP)

(72) Inventors: Yasuhiro Ueda, Kofu (JP); Yoshinori Hishikawa, Zhejiang (CN)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 272 days.

(21) Appl. No.: 14/872,959

(22) Filed: Oct. 1, 2015

(65) Prior Publication Data
US 2016/0015958 A1 Jan. 21, 2016

Related U.S. Application Data

(63) Continuation of application No. PCT/JP2013/002270, filed on Apr. 1, 2013.

(51) Int. Cl.
| | | |
|---|---|---|
| A61M 25/16 | (2006.01) | |
| A61M 25/18 | (2006.01) | |
| *A61M 39/10* | (2006.01) | |
| *A61M 39/26* | (2006.01) | |
| A61M 39/24 | (2006.01) | |

(Continued)

(52) U.S. Cl.
CPC .......... *A61M 39/105* (2013.01); *A61M 39/10* (2013.01); *A61M 39/26* (2013.01); *A61M 5/162* (2013.01); *A61M 2039/0072* (2013.01); *A61M 2039/1072* (2013.01); *A61M 2039/1083* (2013.01); *A61M 2039/2426* (2013.01)

(58) Field of Classification Search
CPC ........ A61M 2039/2426; A61M 39/105; A61M 2039/0072; A61M 2039/1072; A61M 2039/1083; A61M 39/10; A61M 39/26; A61M 5/162

USPC .......................................................... 604/537
See application file for complete search history.

(56) References Cited

U.S. PATENT DOCUMENTS

| | | | |
|---|---|---|---|
| 2011/0160679 A1* | 6/2011 | Okiyama | A61M 39/045 604/246 |
| 2011/0233435 A1* | 9/2011 | Matsumoto | A61M 39/045 251/192 |

FOREIGN PATENT DOCUMENTS

| | | |
|---|---|---|
| JP | 2005-027877 A | 2/2005 |
| JP | 2010-075684 A | 4/2010 |

(Continued)

OTHER PUBLICATIONS

International Search Report (PCT/ISA/210) dated Jun. 18, 2013, by the Japanese Patent Office as the International Searching Authority for International Application No. PCT/JP2013/002270.

*Primary Examiner* — Jason Flick
(74) *Attorney, Agent, or Firm* — Buchanan Ingersoll & Rooney PC (57) ABSTRACT

A connector includes a housing defining a male connector insertion section into which a male connector is inserted from the outside and an elastic valve body having a slit and blocking the male connector insertion section. The elastic valve body includes a top face having the slit and a bottom face located opposite to the top face. The housing includes a holding section having contact with the top face and the bottom face of the elastic valve body to hold the elastic valve body. The holding section surrounds the slit when the valve body is viewed from the top face. The diameter of a bottom face side holding section having contact with the bottom face is smaller than the diameter of a top face side holding section having contact with the top face.

18 Claims, 8 Drawing Sheets

(51) Int. Cl.
  *A61M 5/162* (2006.01)
  *A61M 39/00* (2006.01)

(56) References Cited

FOREIGN PATENT DOCUMENTS

JP         2010-148757 A    7/2010
WO    WO 2010/073643 A1    7/2010

* cited by examiner

CONNECTOR AND INFUSION SET

CROSS-REFERENCES TO RELATED APPLICATIONS

This application is a continuation of International Application No. PCT/JP2013/002270 filed on Apr. 1, 2013, the entire content of which is incorporated herein by reference.

TECHNICAL FIELD

The present invention generally relates to a connector and an infusion set. In particular, the present invention relates to a connector that is capable of connecting thereto a male connector such as various medical devices and infusion solution containers and an infusion set that uses the connector.

BACKGROUND DISCUSSION

Conventionally, when infusion, blood transfusion, or artificial dialysis is performed, liquid is fed into the body using a medical tube. When another liquid such as a liquid medicine is joined to the liquid inside the tube, a connector that is capable of liquid-tightly connecting a male connector such as a syringe and a luer taper member to the medical tube is used. A male connector such as a syringe and a luer taper member may be called a male luer, and a connector connected to the male luer may be called a female luer.

Such a connector capable of connecting a male connector is disclosed, for example, in Japanese Application Publication No. 2010-148757. This application publication discloses a medical mixed injection port in which a disc-like valve member having a slit is held between a tubular port body and an annular ring so as to be assembled thereto. The application publication discloses a configuration in which a locking projection of the tubular port body and a locking projection of the annular ring are engaged with annular grooves formed on an outer peripheral part on the inner face and an outer peripheral part on the outer face of the valve member in order to firmly fix the valve member to the tubular port body. Accordingly, the valve member is held and supported from both sides in the thickness direction of the peripheral part thereof to fix the valve member.

SUMMARY

However, when opening and closing operations for a valve body as the valve member are repeatedly performed by attachment and detachment of a male connector, the valve body may move from an initially fixed position. Accordingly, even when the male connector is removed, the valve body may disadvantageously remain fallen in the male connector insertion section and may not be restored to the initial position.

The connector and an infusion set disclosed here are able to prevent a valve body from moving from an initially fixed position even when opening and closing operations for the valve body are repeatedly performed by attachment and detachment of a male connector.

The disclosed connector comprises a housing defining a male connector insertion section into which a male connector is insertable from outside, and an elastic valve body that includes a slit and that blocks the male connector insertion section. The elastic valve body includes a top face at which is positioned the slit and a bottom face located opposite to the top face, and the housing includes a holding section that is in contact with the top face and the bottom face of the elastic valve body to hold the elastic valve body. The holding section surrounds the slit when the valve body is viewed from the top face, and the holding section includes a bottom face side holding section in contact with the bottom face of the elastic valve body, wherein the bottom face side holding section that is in contact with the bottom face of the elastic valve body possesses a diameter. The holding section also includes a top face side holding section in contact with the top face of the elastic valve body, with the top face side holding section that is in contact with the top face of the elastic valve body possessing a diameter. The diameter of the bottom face side holding section that is in contact with the bottom face of the elastic valve body being smaller than the diameter of the top face side holding section that is in contact with the top face of the elastic valve body.

The male connector insertion section preferably includes an insertion port having a substantially circular shape and the inner diameter of the insertion port is equal to or smaller than the diameter of the bottom face side holding section.

The male connector insertion section preferably is a hollow section at least a part of which has a substantially cylindrical shape, with the elastic valve body arranged on the hollow section, and the housing including a cap defining at least a part of the hollow section and a holder holding the cap.

The cap preferably includes a top face cap which constitutes the top face side holding section and a bottom face cap which constitutes the bottom face side holding section. The cap may constitute the top face side holding section and the holder may constitute the bottom face side holding section.

The holder preferably defines a liquid flow path, and the liquid flow path communicates with the male connector insertion section.

Another aspect of the of the disclosure here involves an infusion set that includes the connector and a tube to which the connector is attached.

According to another aspect, a connector comprises a housing defining a male connector insertion section into which a male connector is insertable from outside, and an elastic valve body positioned in the housing, wherein the elastic valve body including a slit. The elastic valve body includes top and bottom faces at opposite ends of the elastic valve body, with the slit being provided at the top face of the elastic valve body. The elastic valve body includes a top face annular groove which is open towards the top face of the elastic valve body, and the elastic valve body also includes a bottom face annular groove which is open towards the bottom face of the elastic valve body. The housing comprises a top face side holding section and a bottom face side holding section that together hold the elastic valve body. The top face side holding section of the housing includes a top face projection that is annular in shape and positioned in the top face annular groove, and wherein the top face side holding section possessing a diameter. The bottom face side holding section of the housing includes a bottom face projection that is annular in shape and positioned in the top face annular groove, wherein the bottom face side holding section possessing a diameter. The diameter of the bottom face side holding section is smaller than the diameter of the top face side holding section that is in contact with the top face of the elastic valve body.

The connector and the infusion set disclosed here prevent a valve body from moving from an initially fixed position even when opening and closing operations for the valve body are repeatedly performed by attachment and detachment of a male connector.

DETAILED DESCRIPTION

Hereinbelow, embodiments of a connector and an infusion set representing examples of the inventive connector and infusion set disclosed here will be described with reference to FIGS. 1 to 8. Common members are denoted by identical reference numerals throughout the drawings.

First, one embodiment of the connector disclosed here will be described with reference to FIG. 1 which is a cross-sectional view illustrating the configuration of the connector in the present embodiment.

Figure 1:
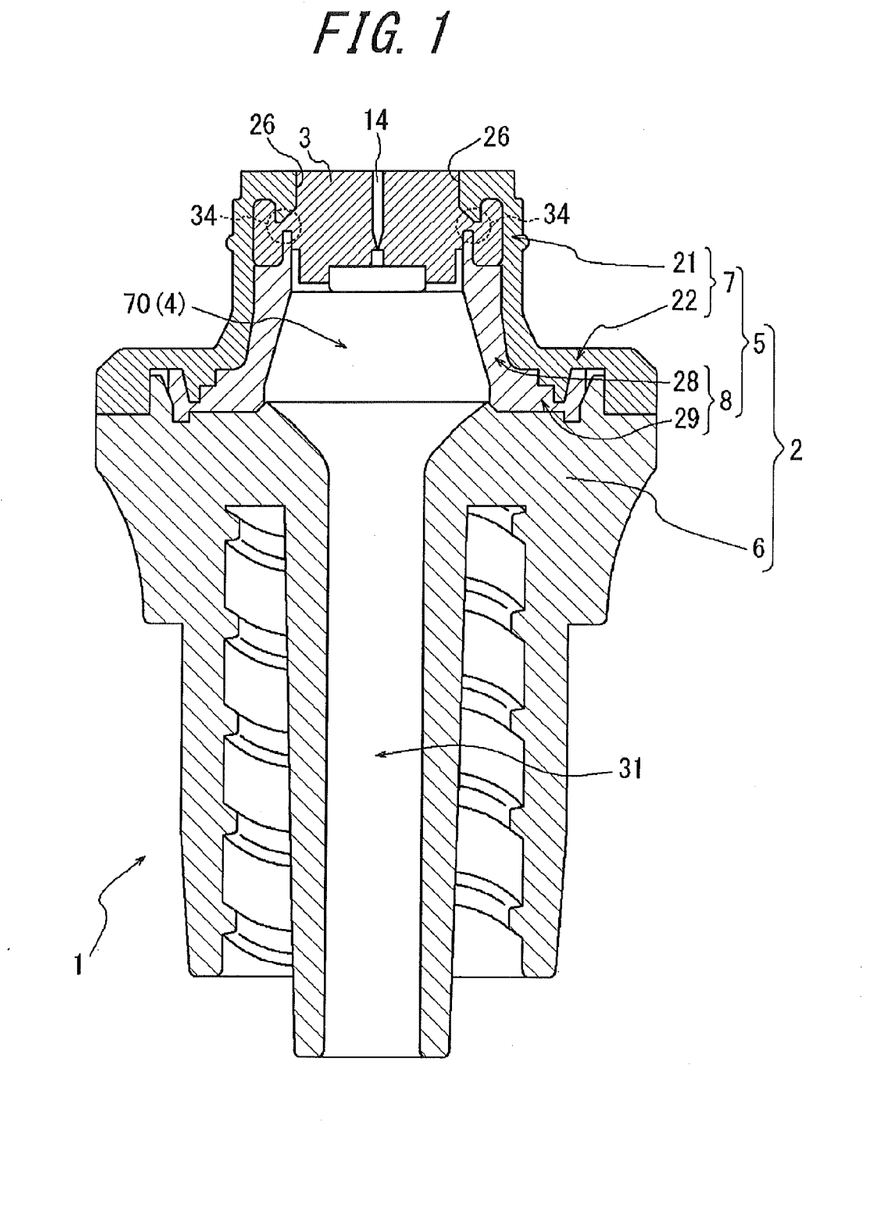
FIG. 1 is a cross-sectional view of a connector representing an embodiment disclosed by way of example.

As illustrated in FIG. 1, the connector 1 is provided with a housing 2 and an elastic valve body 3 which is attached to the housing 2.

The housing 2 is provided with a cap 5 which defines a male connector insertion section 4 into which a male connector 100 (refer to FIG. 7) is inserted from the outside and a holder 6 which supports the cap 5. In the present embodiment, a hollow section 70 defined by the cap 5 corresponds to the male connector insertion section 4.

The cap 5 includes a top face cap 7 and a bottom face cap 8. The outer periphery of the elastic valve body 3 (described below) is compressed and held between the top face cap 7 and the bottom face cap 8 so that the position of the elastic valve body 3 inside the hollow section 70 is fixed. The hollow section 70 as the male connector insertion section 4 is defined by the top face cap 7 and the bottom face cap 8 in the present embodiment.

The holder 6 is a member that supports the top face cap 7 and the bottom face cap 8. In the present embodiment, both the top face cap 7 and the bottom face cap 8 contact the holder 6 so as to be supported by the holder 6. Alternatively, the bottom face cap 8 may be held by the top face cap 7, and only the top face cap 7 may contact the holder 6 so as to be supported by the holder 6. On the other hand, the top face cap 7 may be held by the bottom face cap 8, and only the bottom face cap 8 may contact the holder 6 so as to be supported by the holder 6.

Examples of the materials forming the holder 6 and the top face cap 7 and the bottom face cap 8 as the cap 5 which together form the housing 2 include various resin materials such as polyolefin such as polyethylene, polypropylene, and an ethylene-propylene copolymer; an ethylene-vinyl acetate copolymer (EVA); polyvinyl chloride; polyvinylidene chloride; polystyrene; polyamide; polyimide; polyamide-imide; polycarbonate; poly(4-methyl-1-pentene); ionomer; an acrylic resin; polymethyl methacrylate; an acrylonitrile-butadiene-styrene copolymer (ABS resin); an acrylonitrile-styrene copolymer (AS resin); a butadiene-styrene copolymer; polyester such as polyethylene terephthalate (PET), polybutylene terephthalate (PBT), and polycyclohexane terephthalate (PCT); polyether; polyether ketone (PEK); polyether ether ketone (PEEK); polyether imide; polyacetal (POM); polyphenylene oxide; modified polyphenylene oxide; polysulfone; polyether sulfone; polyphenylene sulfide; polyarylate; aromatic polyester (a liquid crystal polymer); and polytetrafluoroethylene, polyvinylidene fluoride and other fluororesins. A blend or a polymer alloy containing one or more kinds of the above resin materials may also be used. Alternatively, various glass materials, ceramic materials, or metal materials may be used.

The elastic valve body 3 has a slit 14 so that the elastic valve body 3 elastically deforms to open the slit 14 when the male connector 100 (refer to FIG. 7) is attached the connector 1 and to close the slit 14 when the male connector 100 (refer to FIG. 7) is detached from the connector 1. The elastic valve body 3 is arranged to block the male connector insertion section 4 formed by the top face cap 7 and the bottom face cap 8 as the cap 5. Specifically, the elastic valve body 3 is held by a holding section 34 which is constituted from the top face cap 7 and the bottom face cap 8 so that the position of the elastic valve body 3 is fixed.

The elastic valve body 3 is molded and formed to be elastically deformable. Examples of the material forming the elastic valve body 3 include various rubber materials such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, and fluoro rubber; and various thermoplastic elastomers such as a styrene-based thermoplastic elastomer, a polyolefin-based thermoplastic elastomer, a polyvinyl chloride-based thermoplastic elastomer, a polyurethane-based thermoplastic elastomer, a polyester-based thermoplastic elastomer, a polyamide-based thermoplastic elastomer, a polybutadiene-based thermoplastic elastomer, a transpolyisoprene-based thermoplastic elastomer, a fluoro rubber-based thermoplastic elastomer, and a chlorinated polyethylene-based thermoplastic elastomer. A material mixed with one or two or more kinds of these materials may be used.

The hardness of the elastic valve body 3 is preferably 20 to 60° (A hardness). Accordingly, a moderate elastic force can be ensured in the elastic valve body 3. Thus, elastic deformation (described below) can be generated in the elastic valve body 3.

Hereinbelow, each member and a characteristic part by each member in the present embodiment will be described in detail.

Figure 2A:
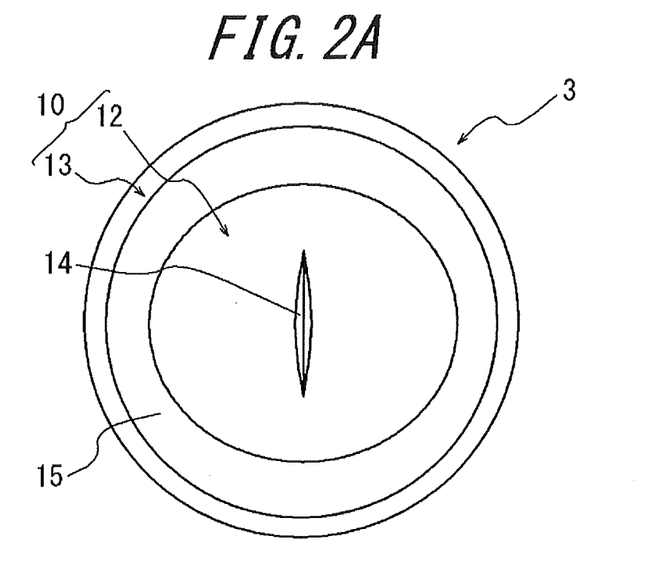
FIG. 2A illustrates a top face of an elastic valve body used in the connector shown in FIG. 1.
Figure 2B:
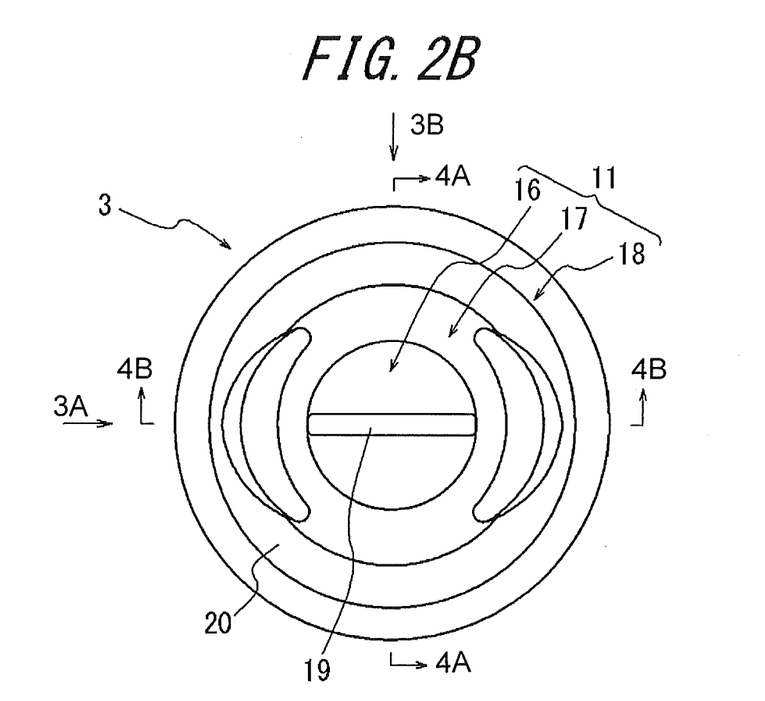
FIG. 2B illustrates a bottom face of the elastic valve body.
Figure 3A:
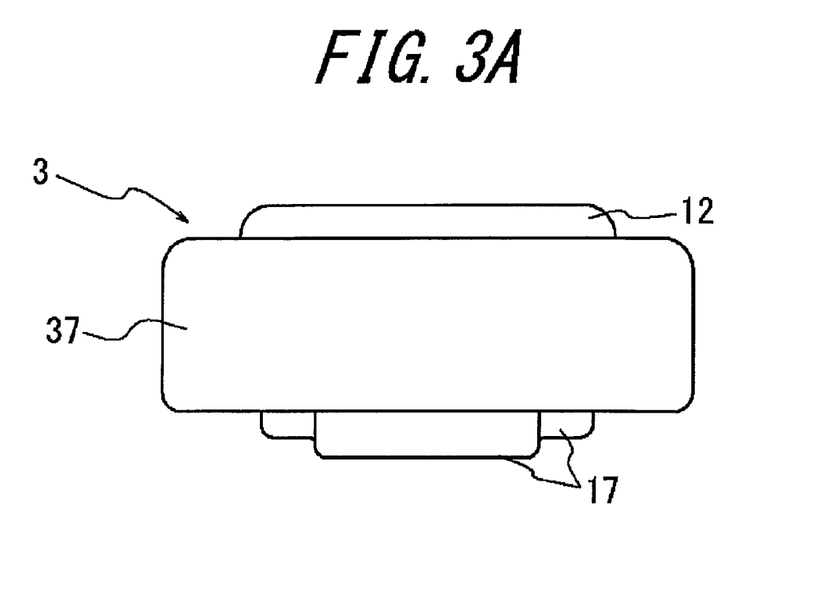
FIG. 3A is a side view of the elastic valve body viewed from direction 3A of FIG. 2B.
Figure 3B:
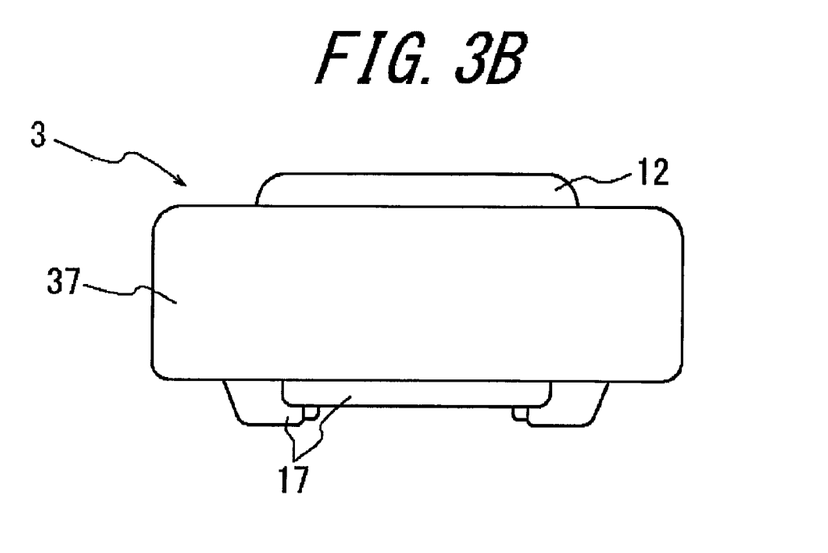
FIG. 3B is a side view of the elastic valve body viewed from direction 3B of FIG. 2B.
Figure 4A:
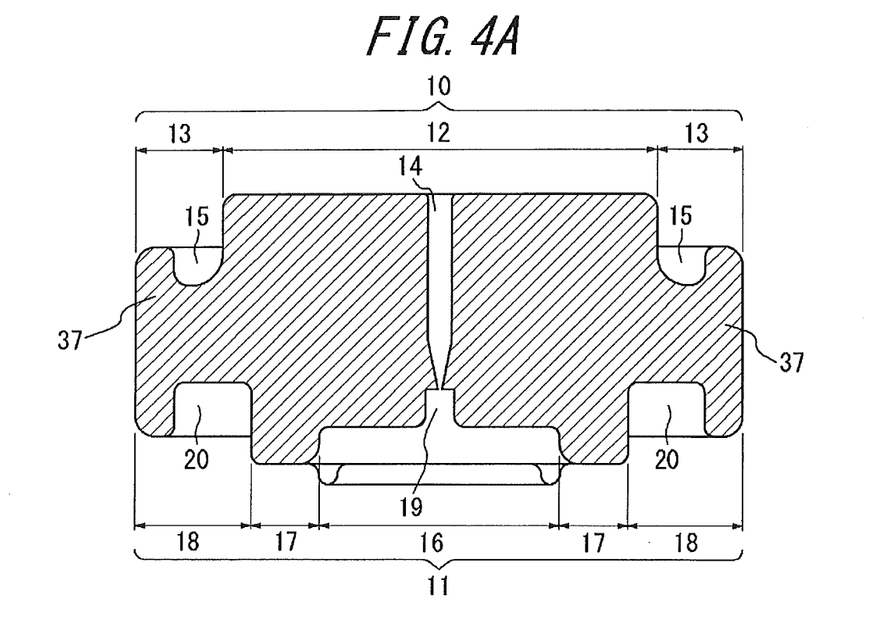
FIG. 4A is a cross-sectional view of the elastic valve body of FIG. 2B taken along the section line 4A-4A in FIG. 2B.
Figure 4B:
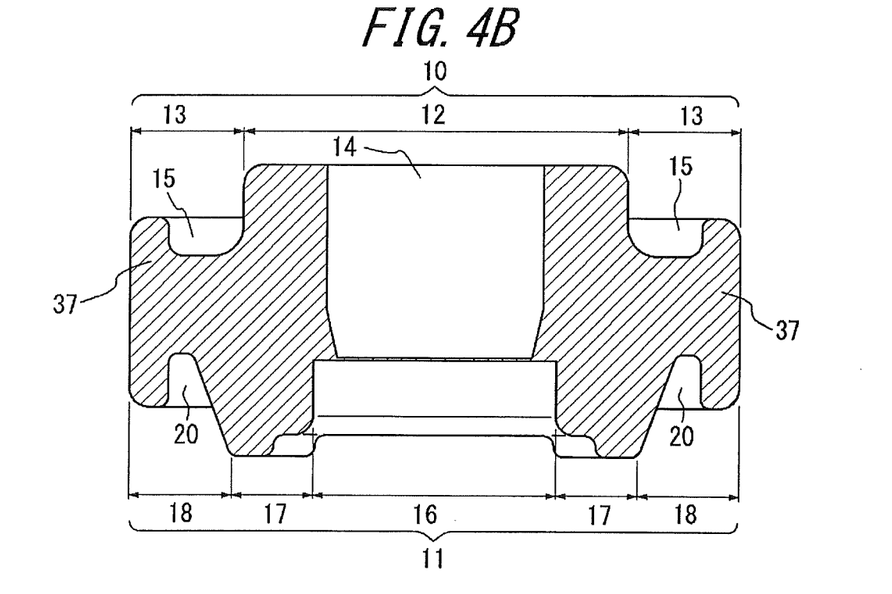
FIG. 4B is a cross-sectional view of the elastic valve body of FIG. 2B taken along the section line 4B-4B in FIG. 2B.

FIGS. 2A and 2B respectively illustrate a top face 10 and a bottom face 11 of the elastic valve body 3 alone. FIGS. 3A and 3B are side views of the elastic valve body 3. FIGS. 4A and 4B are sectional views of the elastic valve body 3 in FIG. 2B.

Figure 5:
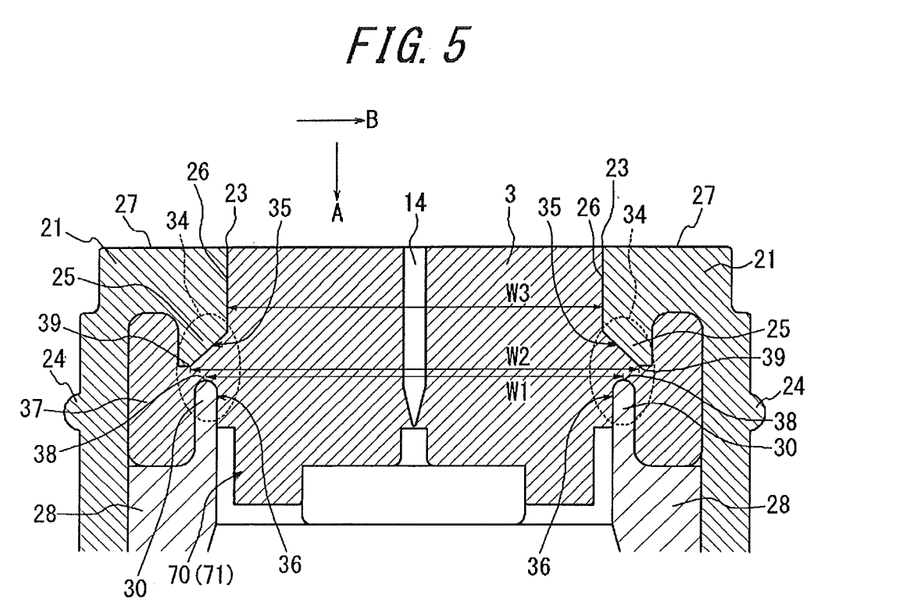
FIG. 5 is an enlarged view of the cross section of the connector in FIG. 1.

As illustrated in FIGS. 2A to 4B, the elastic valve body 3 is a disc-like valve body having a disc-like outer shape. The top face 10 includes a planar top face central region 12 and a top face outer region 13 which is located on the outer side in the radial direction with respect to the top face central region 12. The top face central region 12 has a shape projecting outward (upward in FIGS. 3A to 4B) with respect to the top face outer region 13. The straight slit 14 is formed on the center of the top face central region 12. The slit 14 is molded. The slit 14 does not penetrate the elastic valve body 3 up to the bottom face 11 when molded, but penetrates the elastic valve body 3 up to the bottom face 11 when, for example, the male connector 100 is first inserted after the molding. A process of allowing the slit 14 to penetrate the elastic valve body 3 may be executed as a part of the manufacturing process after the molding is completed. As illustrated in FIG. 2A, the top face central region. 12 is formed in an elliptical shape having a minor axis in a longitudinal direction (extending direction) of the slit 14 and a major axis in a direction perpendicular to the longitudinal direction of the slit 14 when the elastic valve body 3 is not housed in the hollow section 70 (refer to FIG. 1). When the elastic valve body 3 is housed in the hollow section 70, the ellipse of the top face central region 12 is pushed by an inner wall 26 (refer to FIG. 1) on the major axis side of the top face central region 12 to form a circular shape. Accordingly, inner faces of the slit 14 are brought into intimate contact with each other to close the slit 14. For the purpose of facilitating understanding of the configuration, FIG. 1 and FIG. 5 (referred below) illustrate the slit 14 that is not in an intimate-contact and closed state. As illustrated in FIGS. 4A and 4B, a top face annular groove 15 is formed on the top face outer region 13 in a manner surrounding the top face central region 12. As shown in FIG. 5 and described in more detail below, a locking projection 25 (top face projection) of the top face cap 7 enters the top face annular groove 15 and compresses the elastic valve body 3 to constitute a part of the holding section 34. In the top face annular groove 15 of the present embodiment, a groove wall adjacent to the top face central region 12 is formed in a circular arc shape in the sectional view of FIGS. 4A and 4B. Although, in the present embodiment, the top face annular groove 15 is formed at a position adjacent to the top face central region 12, the position of the top face annular groove 15 may be appropriately modified in accordance with the position or the shape of the locking projection 25 of the top face cap 7.

The bottom face 11 of the elastic valve body 3, the bottom face 11 being located opposite to the top face 10, includes a bottom face central region 16, a thick region 17 which is located on the outer side in the radial direction with respect to the bottom face central region 16, and a bottom face outer region 18 which is located on the outer side in the radial direction with respect to the thick region 17. A depression 19 is formed on the bottom face central region 16 at a position facing the slit 14 of the top face 10. For example, when the male connector 100 (refer to FIG. 7) is first inserted, a part located between the tip of the slit 14 formed on the top face 10 and the depression 19 is split, which allows the slit 14 and the depression 19 to communicate with each other. The thick region 17 projects outward (downward in FIGS. 3A to 4B) with respect to the bottom face central region 16 and the bottom face outer region 18. In a configuration that is not provided with the thick region 17, when an excessive load is applied to the elastic valve body 3 during the insertion or removal of the male connector 100 or when the male connector 100 is repeatedly attached and detached, longitudinal ends of the communicating slit 14, the longitudinal ends facing the bottom face 11, may disadvantageously be split. The thick region 17 reinforces the longitudinal ends and thereby makes it possible to avoid the occurrence of the above problem. In the present embodiment, when the elastic valve body 3 is viewed from the bottom face 11, the annular thick region 17 is formed in a manner to surround the depression 19 and thickest at positions on the outer side in the longitudinal direction of the depression 19. Such a configuration makes it possible to prevent the ends of the slit 14 from splitting and to ensure both an excellent insertability of the male connector into the elastic valve body 3 and maintenance of the elastic restoring force of the elastic valve body 3. A bottom face annular groove 20 is formed on the bottom face outer region 18 in a manner surrounding the thick region 17. As described in more detail below, a locking projection 30 (bottom face projection) of the bottom face cap 8 possesses an annular shape and enters or is positioned in the bottom face annular groove 20 and compresses the elastic valve body 3 to constitute a part of the holding section 34 (refer to FIG. 5).

FIG. 5 is an enlarged sectional view illustrating a state in which the elastic valve body 3 is held between the top face cap 7 and the bottom face cap 8. The configurations of the top face cap 7, the bottom face cap 8, and the holder 6 will be described below with reference to FIGS. 1 and 5.

As illustrated in FIG. 1, the top face cap 7 includes a substantially cylindrical hollow barrel 21 and a flange 22 which is formed on or located at one end of the hollow barrel 21. As illustrated in FIG. 5, a substantially circular insertion port 23 is formed on an upper face (upper face in FIG. 5) on the other end of the hollow barrel 21 and the male connector 100 is inserted into the insertion port 23 from the outside. A screw thread 24 is formed on the outer peripheral face of the hollow barrel 21 so as to be screwed with a lock connector defined by ISO 594. The flange 22 is a region integrally molded with the hollow barrel 21. The flange 22 is engaged with the holder 6 (described below) so that the top face cap 7 is held by the holder 6.

As illustrated in FIG. 5, the locking projection 25 is formed on an inner wall of the hollow barrel 21 at a position near the insertion port 23. The locking projection 25 possesses an annular shape, projects in an insertion direction A of the male connector 100 and enters or is positioned in the top face annular groove 15 of the elastic valve body 3 to compress the elastic valve body 3. The inner wall 26 formed between the insertion port 23 and the locking projection 25 contacts the top face central region 12 of the elastic valve body 3 when the male connector 100 is not inserted and contacts the male connector 100 when the male connector 100 is inserted (refer to FIG. 7). That is, when the male connector 100 is not inserted, the top face central region 12 is fitted into a space surrounded by the inner wall 26. On the other hand, when the male connector 100 is inserted, the male connector 100 is fitted with the top face cap 7 through the cylindrical inner wall 26. Although the inner wall 26 in the present embodiment has a cylindrical shape parallel to the insertion direction A, the inner wall 26 may have a tapered shape whose inner diameter is gradually reduced in the insertion direction A corresponding to the outer shape of the male connector 100.

The upper face of the hollow barrel 21 has the insertion port 23 and a planar edge 27 which surrounds the insertion port 23. When the top face central region 12 of the elastic valve body 3 is fitted into the space surrounded by the inner wall 26, that is, when the male connector 100 is not inserted, the top face central region 12 of the elastic valve body 3 is housed up to the position (height) of the insertion port 23, and the top face central region 12 of the elastic valve body 3 and the edge 27 of the top face cap 7 form the same plane. Accordingly, no step is formed between the top face central region 12 and the edge 27. Thus, in a wiping operation for disinfection which is typically performed by a user immediately before the insertion of the male connector 100, the entire top face central region 12 can be easily wiped. As a result, the valve body 3 can be maintained in a sanitary condition without various germs and foreign substances left therein.

As illustrated in FIG. 1, similarly to the top face cap 7, the bottom face cap 8 includes a substantially cylindrical hollow barrel 28 and a flange 29 which is formed on one end of the hollow barrel 28. The locking projection 30 is formed on the other end of the hollow barrel 28. The locking projection 30 projects in a direction opposite to the insertion direction A of the male connector 100 and enters the bottom face annular groove 20 of the elastic valve body 3 to compress and hold the elastic valve body 3 (refer to FIG. 5).

The bottom face cap 8 is ultrasonic-bonded to the inner face of the hollow barrel 21 and/or the lower face (lower face in FIG. 1) of the flange 22 of the top face cap 7 and thereby held by the top face cap 7. Further, the position of the bottom face cap 8 is fixed by supporting the flange 29 of the bottom face cap 8 by the holder 6 (described below).

As illustrated in FIG. 1, the holder 6 supports the top face cap 7 and the bottom face cap 8 and defines a substantially cylindrical liquid flow path 31 inside the holder. The holder 6 of the present embodiment has direct contact with the top face cap 7 and the bottom face cap 8 to support both of them. Alternatively, for example, the holder 6 may have direct contact with only the bottom face cap 8 without contacting the top face cap 7, and the top face cap 7 may contact the bottom face cap 8 so as to be supported by the bottom face cap 8. That is, the holder 6 may have direct contact with either the top face cap 7 or the bottom face cap 8 to support, and may not have direct contact with the other one. The members having direct contact with each other are preferably bonded to each other by, for example, ultrasonic bonding.

When the male connector 100 is not inserted, the hollow section 70 (the male connector insertion section 4) defined by the top face cap 7 and the bottom face cap 8 communicates with the liquid flow path 31. When the male connector 100 is inserted into the connector 1, a tip 32 of the male connector 100 passes through the hollow section 70 and enters the inside of the liquid flow path 31 or the vicinity of the liquid flow path 31. Accordingly, a liquid flow path inside the male connector 100 is brought to communicate with the liquid flow path 31 of the holder 6.

Figure 6:
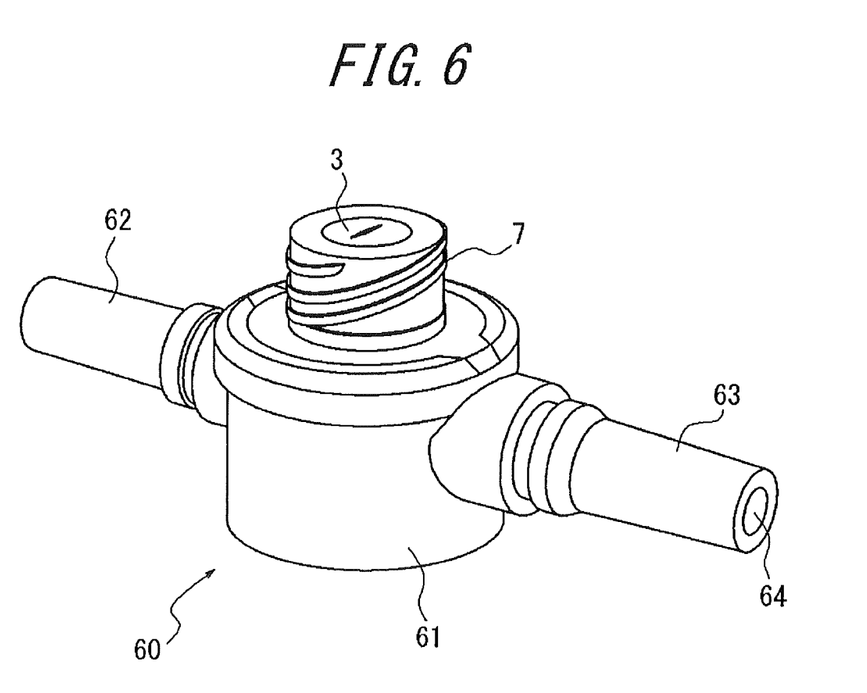
FIG. 6 is a diagram illustrating a holder that has a shape different from the shape of a holder of FIGS. 1 and 5.

Although the holder 6 of the present embodiment has a substantially cylindrical outer shape having a screw thread for a lock connector on the inner peripheral face of the holder 6 and further has a male luer section on the hollow section of the holder 6, the shape of the holder 6 is not limited to such a shape. Various holders may be used and the shape of the holder 6 may be appropriately modified in accordance with the purpose of use of a user. For example, a holder 60 as illustrated in FIG. 6 may be used. The holder 60 is a so-called T port and provided with a holder main body 61 which includes a housing having a substantially cylindrical hollow inside of the holder 60, and a cylindrical first tube connection port 62 and a cylindrical second tube connection port 63 which project from the outer peripheral face of the holder main body 61. The hollow inside of the holder main body 61 serves as a part of a liquid flow path 64 which extends from the first tube connection port 62 through the second tube connection port 63. The top face cap 7 and the bottom face cap 8 (not illustrated in FIG. 6) are supported on an outer wall of the holder 60. The holder 60 illustrated in FIG. 6 differs from the holder 6 in the shape of the liquid flow path inside thereof and the outer shape corresponding to the shape of the liquid flow path. On the other hand, the elastic valve body 3, the top face cap 7, and the bottom face cap 8 described above can be used also in the holder 60.

Next, the configuration of compressing and holding the elastic valve body 3 by the top face cap 7 and the bottom face cap 8 will be described in detail.

As illustrated in FIG. 5, the elastic valve body 3 is attached in a manner to block the hollow section 70 defined by the hollow barrel 21 of the top face cap 7 and the hollow barrel 28 of the bottom face cap 8. Specifically, the elastic valve body 3 is arranged in a part of the hollow section 70 in which a substantially cylindrical hollow section 71 is formed. More specifically, the locking projection 25 of the top face cap 7 enters the top face annular groove 15 of the elastic valve body 3, the locking projection 30 of the bottom face cap 8 enters the bottom face annular groove 20 of the elastic valve body 3, and the elastic valve body 3 is compressed from the top face 10 and the bottom face 11 to form the holding section 34 to fix the elastic valve body 3 so as to be located inside the hollow section 70. The holding section 34 includes a top face side holding section 35 which contacts the top face 10 of the elastic valve body 3 and a bottom face side holding section 36 which contacts the bottom face 11 of the elastic valve body 3. The holding section 34 is formed in a substantially circular and annular shape so as to surround the slit 14 when the elastic valve body 3 is viewed from the top face 10. Here, "when viewed from the top face 10" does not mean whether an actual visual observation is possible, but means when the top face side holding section 35 and the bottom face side holding section 36 are projected on a virtual plane viewed from the top face 10.

A held section 37 which is a part of the elastic valve body 3, the part being located on the outer side in the radial direction with respect to the annular holding section 34, is surrounded and held by a part of the inner wall of the top face cap 7 and a part of the outer wall of the bottom face cap 8 on the periphery of the bottom face cap 8.

A diameter W1 of the bottom face side holding section 36 is shorter (less) than a diameter W2 of the top face side holding section 35. When viewed from the top face 10, both the top face holding section 35 and the bottom face holding section 36 have substantially circular shapes having the same center point. Thus, when W1 and W2 satisfy the above relationship, end points (points on the circumference) that define the diameter W1 of the bottom face side holding section 36 are located closer to the center point than end points that define the diameter W2 of the top face side holding section 35 in a radial direction B (a direction perpendicular to the male connector insertion direction A).

Here, "the diameter W1 of the bottom face side holding section 36" indicates the diameter of a circle that is defined by the most projecting position in the locking projection 30 of the bottom face cap 8 in a direction opposite to the male connector insertion direction A. Further, "the diameter W2 of the top face side holding section 35" indicates the diameter of a circle that is defined by the most projecting position in the locking projection 25 of the top face cap 7 in the male connector insertion direction A. When there are two or more most projecting positions, each of the above diameters indicates the diameter of a circle that is defined by points located closest to the center point in the radial direction B. For example, when the most projecting position is a flat plane, since the plane includes countless points, each of the above diameters indicates the diameter of a circle that is defined by an end of the plane closest to the center point.

Based on the above definition, in the present embodiment, the position that defines the diameter W1 of the bottom face side holding section 36 is a circular arc tip 38 in the locking projection 30, and the position that defines the diameter W2 of the top face side holding section 35 is an apex 39 in the locking projection 25.

When the diameter W2 of the top face side holding section 35 and the diameter W1 of the bottom face side holding section 36 satisfy the above relationship, the bottom face side holding section 36 is located on the inner side with respect to the top face side holding section 35. Thus, even when the elastic valve body 3 elastically deforms to be pushed into the inner side of the connector 1 during the insertion of the male connector 100, a force applied to the locking projection 30 from the elastic valve body 3 is larger than that when the above positional relationship is not employed. Accordingly, a frictional force between the elastic valve body 3 and the locking projection 30 increases to reduce a tension applied to the held section 37. As a result, it is possible to prevent the elastic valve body 3 from moving in a direction in which the elastic valve body 3 comes off the holding section 34.

As described above, when the top face central region 12 of the elastic valve body 3 is housed in the insertion port 23, and the top face central region 12 of the elastic valve body 3 and the edge 27 of the top face cap 7 form the same plane with the male connector 100 not inserted, there is no step between the top face central region 12 of the elastic valve body 3 and the edge 27 of the top face cap 7. Thus, it is easy to wipe the top face central region 12. However, since the connector 1 is repeatedly used, when the male connector 100 is repeatedly inserted and removed, the position of the held section 37 is slightly moved by the tension applied to the elastic valve body 3. Accordingly, the elastic valve body 3 falls into the inner side of the hollow section 70 from the plane position of the edge 27 when the male connector is not inserted to form a step between the top face central region 12 and the edge 27. As a result, there is a problem in the restorability, specifically, in that the elastic valve body 3 is not restored to an initially placed position.

When such a problem occurs, it is difficult to remove foreign substances and various germs accumulated on the step by wiping disinfection with, for example, alcohol. Thus, there is concern about sanitation of the elastic valve body 3. Further, since the elastic valve body 3 moves from the initial position, the elastic restoring force of the penetrating slit 14 may be reduced. Therefore, there is also concern about a deterioration in the sealing performance for an infusion solution by the elastic valve body 3.

The connector disclosed here makes it possible to maintain the top face central region 12 of the elastic valve body 3 and the edge 27 of the top face cap 7 on the same plane even when the connector 1 is repeatedly used by defining the positional relationship between the top face side holding section and the bottom face side holding section compared to a configuration in which such a positional relationship is not employed.

Next, an engagement relationship between the top face cap 7 and the bottom face cap 8 when the elastic valve body 3 is held between the top face cap 7 and the bottom face cap 8 will be described. An outer wall of the hollow barrel 28 of the bottom face cap 8 contacts an inner wall of the hollow barrel 21 of the top face cap 7. A space surrounding the held section 37 of the elastic valve body 3 is defined by a part of the inner wall of the hollow barrel 21 and a part of the outer wall of the hollow barrel 28 on the outer side in the radial direction B with respect to the locking projection 25 and the locking projection 30.

An outer wall (upper face in FIG. 1) of the flange 29 of the bottom face cap 8 is engaged with an inner wall (lower face in FIG. 1) of the flange 22 of the top face cap 7.

The connector 1 with the male connector 100 not inserted has been mainly described above. Hereinbelow, each member of the connector 1 when the male connector is inserted will be described.

Figure 7:
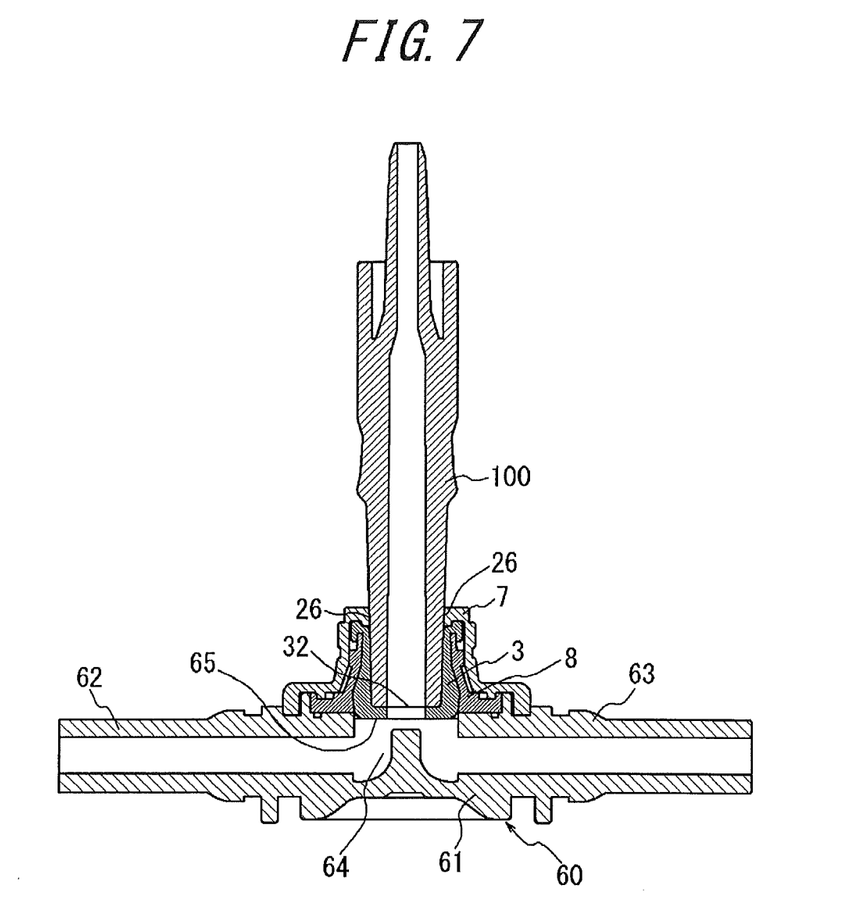
FIG. 7 is a diagram illustrating a state in which a male connector is inserted into the connector.

FIG. 7 illustrates the male connector 100 inserted into the connector 1. Although FIG. 7 illustrates a configuration in which the holder 60 is used instead of the holder 6, the holder 6 may also be used. The elastic valve body 3, the top face cap 7, and the bottom face cap 8 have the same configurations as those of the connector 1 described above.

When the male connector 100 is inserted into the connector 1, the tip of the male connector 100 pushes the elastic valve body 3 into the connector 1 to cause the elastic valve body 3 to elastically deform, and reaches the inside of the liquid flow path 64 inside the holder main body 61 or the vicinity of the holder main body 61 through the penetrating slit 14.

The elastic valve body 3 elastically deforms by the insertion of the male connector 100 and enters a gap between the inner wall of the bottom face cap 8 and the outer wall of the male connector 100, so that the elastic valve body 3 is brought into intimate contact with the outer face of the male connector 100. Accordingly, leakage of liquid from the connector 1 to the outside is prevented.

The tip 32 of the male connector 100 collides with or contacts a positioning section 65 which is formed on the upper face of the holder main body 61 with the elastic valve body 3 interposed between the tip 32 and the positioning section 65, so that the male connector 100 is positioned in the insertion direction A. Although the elastic valve body 3 is interposed between the tip 32 and the positioning section 65, the liquid flow path inside the male connector 100 communicates with the liquid flow path 64 through the slit 14 which penetrates the elastic valve body 3.

As illustrated in FIG. 5, an inner diameter W3 of the substantially circular insertion port 23 which is edged with (intersects with) the edge 27 of the top face cap 7 is equal to or smaller than the diameter W1 of the bottom face side holding section 36. When the male connector 100 is inserted, the inner wall 26 of the top face cap 7 comes into contact with the outer face of the male connector 100 as described above, and the male connector 100 is thereby locked to the connector 1. When W1≥W3 is satisfied, a space can be ensured between the inner wall of the bottom face cap 8 and the outer wall of the male connector 100 so as to allow the elastic valve body 3 to elastically deform and enter the space. In the present embodiment, the length of W1 is set within the range of 4.6 mm to 5.5 mm taking into consideration the size of the hollow section 70 (the inner diameters of the hollow barrels 21, 28) into which the male connector 100 defined by ISO 594 (having a tapered shape whose outer diameter is reduced by 6% per 1 mm toward the tip) can be inserted and an outer diameter that enables a lock connector defined by ISO 594 to be screwed with the outer peripheral face of the hollow barrel 21. In this manner, the length of each of W1 to W3 is restricted under the requirements of ISO 594. Thus, it is difficult to ensure a sufficient size of the held section 37, and the held section 37 rather easily moves and comes off the holding section 34. Therefore, setting W2≥W1 as described above is particularly effective.

In the present embodiment, the holding section 34 includes the top face cap 7 and the bottom face cap 8 which constitute the cap 5. As another embodiment, for example, the bottom face cap 8 and the holder 6 may be configured as a single member, the holder 6 itself may have a function of the bottom face cap 8, and the top face cap 7 and the holder 6 which constitute the cap 5 may form the holding section 34. Specifically, the top face cap 7 constitutes the top face side holding section 35, and the holder 6 constitutes the bottom face side holding section 36. In this case, the hollow section 70 as the male connector insertion section 4 is defined by the top face cap 7 and the holder 6. Also in such a case, the holder 6 supports the top face cap 7 and defines the liquid flow path 31 communicating with the hollow section 70.

Alternatively, the bottom face cap 8 and the holder 60 may be configured as a single member using the shape of the holder 60 instead of the shape of the holder 6. Specifically, the top face cap 7 constitutes the top face side holding section 35, and the holder 60 constitutes the bottom face side holding section 36. In this case, the hollow section 70 as the male connector insertion section 4 is defined by the top face cap 7 and the holder 60. The holder 60 supports the top face cap 7 and defines a part of the liquid flow path 64 communicating with the hollow section 70.

In this manner, in the connector disclosed here, at least any two of the members which constitute the housing may constitute the holding section which holds the elastic valve body, and the members are not limited to the top face cap, the bottom face cap, and the holder.

At last, an embodiment of an infusion set 80 which uses the connector 1 disclosed here will be described with reference to FIG. 8. Here, the infusion set 80 which includes the connector 1 using the holder 60 described above will be described. However, the shape of the holder may be appropriately modified in accordance with the purpose of use of the infusion set, and the shape of the holder 6 may be employed to constitute the infusion set.

Figure 8:
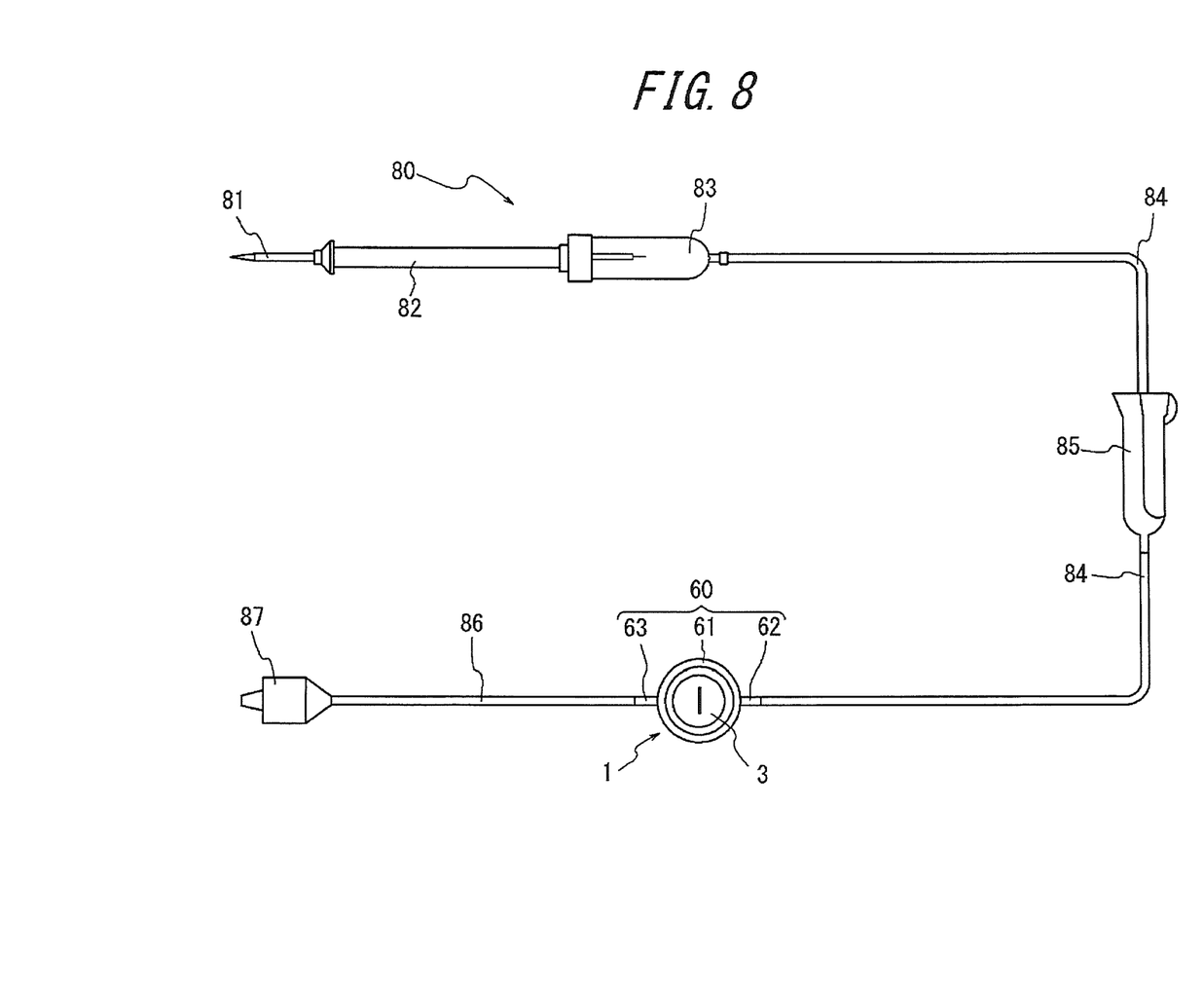
FIG. 8 is a diagram illustrating an infusion set.

As illustrated in FIG. 8, the infusion set 80 is provided with a bottle needle 81 which is inserted into an infusion solution bag in which is stored liquid, a first tube 82 which is coupled to the base of the bottle needle 81 and forms a liquid flow path, a drip infusion cylinder 83 which is coupled to the downstream side of the liquid flow path of the first tube 82, a second tube 84 which is coupled to the drip infusion cylinder 83 and forms a liquid flow path for liquid discharged from the drip infusion cylinder 83, a clamp 85 which is attached to the outer peripheral face of the second tube 84 and capable of adjusting the flow rate of liquid passing through the second tube 84, the connector 1 which is provided with the holder 60 which includes a first tube connection port 62 coupled to an end of the second tube 84, the end being located on the liquid flow path downstream side with respect to the placement position of the clamp 85, a third tube 86 which is coupled to a second tube connection port 63 of the connector 1 and forms a liquid flow path, and a lock connector 87 which is coupled to a downstream end of the liquid flow path of the third tube 86.

In the infusion set 80, the third tube 86 couples the connector 1 to the lock connector 87. Alternatively, another connector 1 may be added between the connector 1 and the lock connector 87, and a tube for coupling may also be added. Further, another clamp 85 may be added or the clamp 85 may be arranged at another position. The elements of the infusion set 80 and the positions of the elements may be appropriately modified and combined by a person skilled in the art in accordance with the purpose of use of a user, and are not limited to the configuration of the infusion set 80 described above.

The first to third tubes 82, 84, 86 and the elements connected to these tubes are preferably coupled by lock connectors.

Since the infusion set 80 is provided with the connector 1, a liquid different from a liquid from the infusion solution bag to which the bottle needle 81 is connected can be supplied to the infusion line through the connector 1. Thus, it is not necessary to provide different infusion lines for the respective liquids to be supplied to the body.

The present invention is not limited to the configuration specified by the above embodiments, and various modifications may be made within the range of the subject matter of the invention described in the claims.

The "top face" of the elastic valve body 3 used herein indicates a face at least a part of which is exposed to the outside in the elastic valve body 3. The "top face cap" indicates a cap that has contact with the "top face" of the elastic valve body 3. Similarly, the "bottom face cap" indicates a cap that has contact with the bottom face of the elastic valve body 3.

The detailed description above describes embodiments and modifications of a connector and an infusion set representing examples of the connector and an infusion set disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A connector comprising:
    a housing defining a male connector insertion section into which a male connector is insertable from outside;
    an elastic valve body that includes a slit and that blocks the male connector insertion section;
    the elastic valve body including a top face at which is positioned the slit and a bottom face located opposite to the top face,
    the housing including a holding section that is in contact with the top face and the bottom face of the elastic valve body to hold the elastic valve body;
    the holding section surrounding the slit when the valve body is viewed from the top face, the holding section including a bottom face side holding section in contact with the bottom face of the elastic valve body, the bottom face side holding section that is in contact with the bottom face of the elastic valve body possessing a diameter;
    the holding section also including a top face side holding section in contact with the top face of the elastic valve body, the top face side holding section that is in contact with the top face of the elastic valve body possessing a diameter; and
    the diameter of the bottom face side holding section that is in contact with the bottom face of the elastic valve body being smaller than the diameter of the top face side holding section that is in contact with the top face of the elastic valve body.

2. The connector according to claim 1, wherein the male connector insertion section includes an insertion port possessing a circular shape, the insertion port possessing an inner diameter equal to or smaller than the diameter of the bottom face side holding section.

3. The connector according to claim 1, wherein
the male connector insertion section is a hollow section at least a part of which possesses a cylindrical shape;
the elastic valve body is arranged on the hollow section; and
the housing includes a cap defining at least a part of the hollow section and a holder holding the cap.

4. The connector according to claim 3, wherein the cap includes a top face cap which constitutes the top face side holding section and a bottom face cap which constitutes the bottom face side holding section.

5. The connector according to claim 3, wherein the cap constitutes the top face side holding section and the holder constitutes the bottom face side holding section.

6. The connector according to claim 3, wherein the holder defines a liquid flow path, and the liquid flow path communicates with the male connector insertion section.

7. A connector comprising:
a housing defining a male connector insertion section into which a male connector is insertable from outside;
an elastic valve body positioned in the housing, the elastic valve body including a slit;
the elastic valve body including top and bottom faces at opposite ends of the elastic valve body, the slit being provided at the top face of the elastic valve body;
the elastic valve body including a top face annular groove which is open towards the top face of the elastic valve body, the elastic valve body also including a bottom face annular groove which is open towards the bottom face of the elastic valve body;
the housing comprising a top face side holding section and a bottom face side holding section that together hold the elastic valve body;
the top face side holding section of the housing including a top face projection that is annular in shape and positioned in the top face annular groove, the top face side holding section possessing a diameter;
the bottom face side holding section of the housing including a bottom face projection that is annular in shape and positioned in the top face annular groove, the bottom face side holding section possessing a diameter; and
the diameter of the bottom face side holding section being smaller than the diameter of the top face side holding section that is in contact with the top face of the elastic valve body.

8. The connector according to claim 7, wherein the elastic valve body includes a held section which is positioned radially outside of the top face annular projection and the bottom face annular projection.

9. The connector according to claim 7, wherein the housing includes a top face cap and a bottom face cap that are separate elements in contact with one another, the top face cap being comprised of a hollow barrel and a flange at one end of the hollow barrel, the flange projecting radially outwardly of the hollow barrel, the top face annular projection being a part of the hollow barrel.

10. The connector according to claim 9, wherein the bottom face cap is comprised of a hollow barrel and a flange at one end of the hollow barrel of the bottom face cap, the flange at one end of the hollow barrel of the bottom face cap projecting radially outwardly of the hollow barrel of the bottom face cap, the bottom face annular projection being a part of the hollow barrel of the bottom face cap.

11. The connector according to claim 7, wherein the housing includes a top face cap and a bottom face cap that are separate elements in contact with one another, the bottom face cap being comprised of a hollow barrel and a flange at one end of the hollow barrel, the flange projecting radially outwardly of the hollow barrel, the bottom face annular projection being a part of the hollow barrel.

12. The connector according to claim 7, wherein the male connector insertion section includes an insertion port possessing a circular shape, the insertion port possessing an inner diameter equal to or smaller than the diameter of the bottom face side holding section.

13. The connector according to claim 7, wherein the male connector insertion section is hollow, at least a part of the hollow male connector insertion section possessing a cylindrical shape, and the elastic valve body being positioned in the part of the hollow male connector insertion section possessing the cylindrical shape.

14. The connector according to claim 7, wherein the housing includes a hollow cap and a holder that are separate members, the hollow cap holding the cap, the elastic valve body being positioned in the hollow cap.

15. The connector according to claim 14, wherein the cap includes a top face cap and a bottom face cap which are separate elements in contact with one another, the top face annular projection being a part of the top face cap, and the bottom face annular projection being a part of the bottom face cap.

16. The connector according to claim 14, wherein the cap constitutes the top face side holding section and the holder constitutes the bottom face side holding section.

17. The connector according to claim 14, wherein the holder defines a liquid flow path, and the liquid flow path communicates with the male connector insertion section.

18. An infusion set comprising:
a connector; and
a tube to which the connector is attached;
the connector comprising:
a housing defining a male connector insertion section into which a male connector is insertable from outside;
an elastic valve body that includes a slit and that blocks the male connector insertion section;
the elastic valve body including a top face at which is positioned the slit and a bottom face located opposite to the top face,
the housing including a holding section that is in contact with the top face and the bottom face of the elastic valve body to hold the elastic valve body;
the holding section surrounding the slit when the valve body is viewed from the top face, the holding section including a bottom face side holding section in contact with the bottom face of the elastic valve body, the bottom face side holding section that is in contact with the bottom face of the elastic valve body possessing a diameter;
the holding section also including a top face side holding section in contact with the top face of the elastic valve body, the top face side holding section that is in contact with the top face of the elastic valve body possessing a diameter; and
the diameter of the bottom face side holding section that is in contact with the bottom face of the elastic valve body being smaller than the diameter of the top face side holding section that is in contact with the top face of the elastic valve body.

\* \* \* \* \*